(12) United States Patent
Ábrahám et al.

(10) Patent No.: US 6,482,819 B1
(45) Date of Patent: Nov. 19, 2002

(54) 2,3-BENZODIAZEPINE DERIVATIVES

(75) Inventors: Gizella Ábrahám, Budapest (HU); Emese Csuzdi, Budapest (HU); Sándor Sólyom, Budapest (HU); Pál Berzsenyi, Budapest (HU); István Tarnawa, Budapest (HU); Ferenc Andrási, Budapest (HU); István Ling, Budapest (HU); Tamás Hámori, Budapest (HU); Katalin Horváth, Budapest (HU); Imre Moravcsik, Budapest (HU); István Pallagi, Budapest (HU); Antal Simay, Budapest (HU)

(73) Assignee: Gyogyszerkutato Intezet Kft., Budapest (HU)

( * ) Notice: Subject to any disclaimer, the term of this patent is extended or adjusted under 35 U.S.C. 154(b) by 0 days.

(21) Appl. No.: 09/463,440

(22) PCT Filed: Jul. 27, 1998

(86) PCT No.: PCT/HU98/00071

§ 371 (c)(1),
(2), (4) Date: Apr. 10, 2000

(87) PCT Pub. No.: WO99/06408

PCT Pub. Date: Feb. 11, 1999

(30) Foreign Application Priority Data

Jul. 31, 1997 (HU) .............................. 97 01325

(51) Int. Cl.⁷ .................... A61K 31/551; C07D 487/04
(52) U.S. Cl. .................. 514/211.08; 540/562
(58) Field of Search ...................... 514/211.08; 540/562

(56) References Cited

U.S. PATENT DOCUMENTS

| | | | |
|---|---|---|---|
| 5,459,137 A | 10/1995 | Andrási et al. | 514/220 |
| 5,756,495 A | 5/1998 | Hámori et al. | 514/220 |
| 5,795,886 A | 8/1998 | Anderson et al. | 514/220 |
| 6,323,197 B1 | 11/2001 | Csuzdi et al. | 514/219 |

*Primary Examiner*—John M. Ford
(74) *Attorney, Agent, or Firm*—Keil & Weinkauf

(57) ABSTRACT

2,3-Benzodiazepines of formula (I), their stereoisomers and acid addition salts,

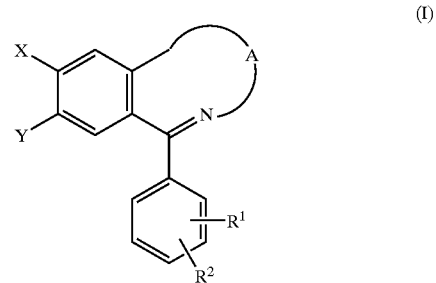

(I)

wherein the variables have the meaning given in the specification, and pharmaceutical compositions containing them which are suitable for treating conditions associated with muscle spasms, epilepsy as well as acute and chronic forms of neurodegenerative diseases are disclosed.

10 Claims, No Drawings

2,3-BENZODIAZEPINE DERIVATIVES

BACKGROUND OF THE INVENTION

The invention relates to new tricyclic 2,3-benzodiazepine derivatives substituted by halogen atom and to pharmaceutical compositions containing the same.

Among the 2,3-benzodiazepines with dimethoxy or methylenedioxy substitution at the benzene ring several became known for their biological activity and therapeutic use. The Hungarian patent specifications Nos. 155,572, 179,018, 191,702 and 195,788 disclose 7,8-dimethoxy derivatives. These compounds exhibit primarily anxiolytic and/or antidepressant as well as positive inotropic effect. Compounds having methylenedioxy substitution at the same position of the benzene ring are disclosed in the Hungarian patent specifications Nos. 191,698, 191,702, 206,719, in the U.S. Pat. No. 5,459,137 and the published international patent application No. WO 96/04283.

Unlike the former compounds the 2,3-benzodiazepine derivatives substituted with a methylenedioxy group have mainly anticonvulsive, muscle relaxant and neuroprotective effect. In the literature it is widely known that the noncompetitive inhibition of the AMPA receptor constitutes the basis of the action of these compounds [S. D. Donevan et al.: Neuron 10, 51–59 (1993), J. Pharmacol. Exp. Ther. 271, 25–29 (1994), I. Tarnawa et al.: Bioorg. Med. Chem. Lett., 3, 99–104 (1993)].

It is known that in the central nervous system of mammals L-glutamic acid is the most important excitatory neurotransmitter. At pathological conditions the extracellular glutamic acid concentration is pathologically increased causing acute or chronic damage in the neurons of the central nervous system.

The effect of excitatory amino acids (such as glutamic acid) is exerted by the activation of the inotropic (ion channel) and G-protein bound metabotropic receptors. The types of ionotropic glutamate receptors were designated according to the agonists which are suitable for their selective excitation. Accordingly three types of receptors are differentiated: NMDA, AMPA and kainate (formerly quisqualate) receptors which are subdivided into further subgroups [Ann. Rev. Neurosci. 17, 31, (1994)].

It was confirmed that in several acute and chronic diseases where the central nervous system is involved, e. g. epilepsy, diseases with adjuvant muscle spasms and various neurodegenerative diseases, AMPA-type glutamate receptors are playing a major role, and anticonvulsive, muscle relaxant and neuroprotective effect may be achieved by inhibiting the AMPA receptors [Cerebrovasc. Brain Metab. Rev. 6, 225 (1994); Neurology 44, Suppl. 8, S14 (1994); J. Pharmacol. Exp. Ther. 260, 742 (1992)].

The inhibition of AMPA receptor activation may be attained with both competitive and noncompetitive antagonists. The use of noncompetitive antagonists may be generally more advantageous than that of competitive antagonists as they give a higher level of protection at extremely high endogenous concentrations of excitatory amino acids [Epilepsy Res., 15, 179 (1993)].

SUMMARY OF THE INVENTION

Based on the above it was an observation of major importance that the types of 2,3-benzodiazepines, substituted with a methylenedioxy group, described in the introduction, possess anticonvulsive, muscle relaxant and neuroprotective properties due to their noncompetitive AMPA antagonist effect and consequently can be used in therapy as anticonvulsive, antiepileptic agents in acute and chronic neurodegenerative diseases as well as potentially in all diseases where the inhibition of excitatory amino acids is desirable at receptor levels.

Research involving the synthesis and pharmacological investigation of novel 2,3-benzodiazepines designed for therapeutic use revealed that the novel 2,3-benzodiazepine derivatives according to the invention, substituted with halogen on the benzene ring and having a heterocyclic ring fused to the 7-membered ring, possess significant AMPA antagonistic effect and thus can be used for the treatment of the diseases of the central nervous system mentioned above. Furthermore it was found that the novel compounds according to the invention have more advantageous properties than the known compounds.

DETAILED DESCRIPTION OF THE INVENTION

Based on the above the invention relates to novel 2,3-benzo-diazepines of general formula (I), their potential stereoisomers and acid addition salts,

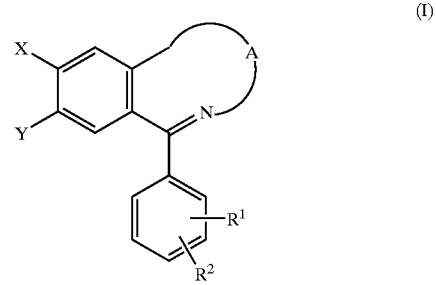

(I)

wherein $R^1$ and $R^2$ represent independently hydrogen, halogen, a $C_{1-4}$ alkyl, $C_{1-4}$ alkoxy, nitro, trifluoromethyl group or a group of general formula $NR^8R^9$, wherein $R^8$ and $R^9$ represent independently hydrogen, a $C_{1-4}$ alkyl group or a group of general formula $-COR^{10}$, wherein $R^{10}$ represents hydrogen, an optionally substituted $C_{1-4}$ alkyl group, $C_{6-10}$ aryl group, $C_{1-4}$ alkoxy group, $C_{3-5}$ cyclo-alkyl group, $C_{2-6}$ alkenyl group, $C_{3-5}$ cycloalkoxy group or a group of general formula $-NR^{11}R^{12}$, wherein $R^{11}$ and $R^{12}$ represent independently hydrogen, a $C_{1-4}$ alkyl group, $C_{3-5}$ cycloalkyl group or $C_{6-10}$ aryl group, X represents hydrogen or chlorine atom, Y represents chlorine or bromine atom, A represents a group of general formula (a), (b), (c) or (d),

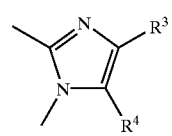

(a)

-continued

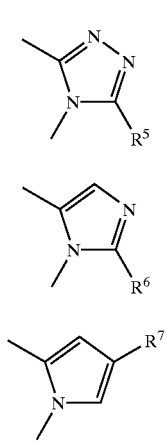

wherein

R³, R⁴, R⁵, R⁶ and R⁷ represent independently hydrogen, a $C_{1-4}$ alkyl group, $C_{3-5}$ cycloalkyl group, $C_{2-4}$ alkenyl group, $C_{2-4}$ alkinyl group or $C_{6-10}$ aryl group which can optionally be substituted by one or more halogen, nitro, alkoxy or amino groups; furthermore heteroaryl group; groups of general formula —COOR¹³ or —CO—NR¹⁴R¹⁵, wherein R¹³ represents hydrogen or $C_{1-4}$ alkyl group, R¹⁴ and R¹⁵ represent independently hydrogen or a $C_{1-4}$ alkyl group or form together with the nitrogen atom a 5 to 7-membered saturated heterocycle which can contain further oxygen, sulfur or nitrogen atoms.

In the groups of general formula (I) the alkyl and alkenyl groups can be both straight and branched groups. The cycloalkyl group can be a cyclopropyl, cyclobutyl or cyclopentyl group. The aryl group can be a phenyl or naphthyl group. The heteroaryl group can be an aromatic heterocyclic group, e.g. thienyl, furyl, pyridyl, etc.

When compounds of general formula (I) have a chiral centrum, the term "isomer" represents both enantiomers, furthermore, due to stereoisomers developing because of particular substitutions, E and Z isomers, diastereomers, tautomers as well as mixtures thereof, e. g. racemates.

The salts of the compounds of general formula (I) are physiologically acceptable salts formed with inorganic and organic acids. Suitable inorganic acids are e.g. hydrochloric acid, hydrobromic acid, phosphoric acid or sulfuric acid. Suitable organic acids are formic acid, acetic acid, maleic and fumaric acid, succinic acid, lactic acid, tartaric acid, citric acid or methanesulfonic acid.

A preferred group of the compounds of general formula (I) of the invention are those of general formula (Ia) wherein X and Y, or at least Y represent a chlorine atom, R¹ represents an amino group in position 4 and R² stands for hydrogen, furthermore one of R³ or R⁴ stands for a methyl group.

Compounds of general formula (I) of the invention are prepared by a) reacting a compound of general formula (II) or (III),

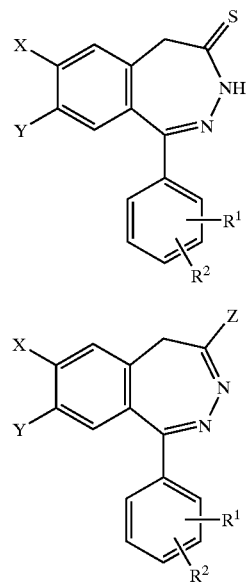

wherein R¹, R², X and Y have the same meaning as above and Z represents a $C_{1-3}$ alkylthio group, with α) an aminoacetal or aminoketal of general formula (IV),

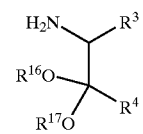

wherein R³ and R⁴ have the same meaning as above, R¹⁶ and R¹⁷ represent independently $C_{1-4}$ alkyl group or together a $C_{2-4}$ alkylene group, the intermediate formed in the reaction is submitted to acidic ring closure resulting in a compound of general formula (I), wherein R¹, R², X and Y have the same meaning as above and (A) represents a group of general formula (a), wherein R³ and R⁴ have the same meaning as above, or β) an acid hydrazide of general formula (V)

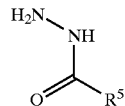

wherein R⁵ has the same meaning as above, or the compounds of general formula (II) or (III) are first reacted with hydrazine hydrate and the resulting intermediates are treated with an acid anhydride, yielding compounds of general formula (I) wherein R¹, R², X and Y have the same meaning as above and (A) represents a group of general formula (b), wherein R⁵ has the same meaning as above, or (b) in a compound of general formula (III), wherein R¹, R², X and Y have the same meaning as above and Z represents a hydroxymethyl group, this latter group is converted into an aminomethyl group which is acylated and closed to a ring, resulting in a compound of general formula (I) wherein (A) represents a group of general formula (c), wherein $R^6$ has the same meaning as above, or (c) a compound of general formula (III), wherein $R^1$, $R^2$, X and Y have the same meaning as above and Z represents a methyl group, is reacted with a compound of general formula (VI),

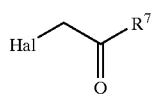

(VI)

wherein $R^7$ has the same meaning as above and Hal represents a chloro or bromo substituent, wherby a compound of general formula (I) is obtained, wherein (A) represents a group of general formula (d), wherein $R^7$ has the same meaning as above, then, if desired, in the compound of general formula (I) obtained by any of the alternative processes the nitro group is reduced or the amino group is acylated, alkylated, or via diazotization substituted by a halogen or hydrogen atom, thus transforming it into an other compound of general formula (I) and/or the stereoisomers are separated and optionally a salt is formed.

The 4-thioxo-2,3-benzodiazepines of general formula (II), used for preparing some of the compounds of the invention, are synthesized by thionating the corresponding 4-oxo-2,3-benzodiazepine derivatives, using advantageously phosphorus pentasulfide or Lawesson reagent, and conducting the reaction in pyridine. The preparation of 4-oxo-2,3-benzodiazepines is known from the literature [F. Gatta. et al.: I] Farmaco Ed. Sc. 40, 942 (1985) and A. Chimirri et al.: J. Med. Chem. 40, 1258 (1997)] and essentially the process reported therein was followed.

Eventually the preparation of the compounds of the invention can be advantageously realized by starting from compounds of general formula (III), wherein Z represents an alkylthio group. In a suitable process 4-(methylthio)-5H-2,3-benzodiazepine derivatives are applied as starting materials which are suitably prepared by methylating compounds of general formula (II). The methylation of compounds of general formula (II) is preferably carried out with e. g. methyliodide in acetone in the presence of an acid binding agent.

Compounds of general formula (I) wherein (A) represents a group of general formula (a) are prepared by condensing the corresponding 4-thioxo compound of general formula (II) in an organic solvent, e. g. ethyleneglycol monomethyl ether, with an α-aminoacetal or -ketal of general formula (IV). The acetal or ketal group can be open or can have a ring structure. In the course of condensation the liberated sulfur is bound by a suitable reagent, preferably e. g. mercuri oxide or silver salts. The resulting intermediate compound is isolated and processed usually as a raw product in the ring closing reaction which is preferably realized by heating in a mixture of ethanol and hydrochloric acid.

The α-aminoacetals or -ketals used as reagents are known in the literature and are prepared accordingly [Jiro Adachi et al.: J. Org. Chem. 37, 221 (1972); Skinzo Kano et al.: Heterocycles 26, 2805 (1987); Org. Synth. 64, 19 (1986)].

Compounds of general formula (I), wherein (A) represents a group of general formula (b), are advantageously prepared by reacting a compound of general formula (III), wherein Z represents a methylthio group, in an organic solvent, e. g. ethyleneglycol monomethyl ether, with an acyl hydrazide, in the presence of catalytic amounts of an acid, e.g. p-toluenesulfonic acid. In this case condensation and ring closure proceed in a single reaction step resulting in the corresponding triazolo-2,3-benzodiazepine.

The same compounds can also be prepared by reacting first the 4-methylthio-2,3-benzodiazepine derivative of general formula (III) with hydrazine hydrate or by a condensation reaction between the corresponding 4-thioxo-benzodiazepine and hydrazine hydrate in the presence of e.g. mercury oxide and the resulting 4-hydrazino-2,3-benzodiazepine derivative is reacted with the chosen acid anhydride yielding the expected triazolo-2,3-benzodiazepine.

Compounds of general formula (I) wherein (A) represents a group of general formula (c) or (d) can be prepared by starting from the corresponding 4-methyl-5H-2,3-benzodiazepines. The latter ones can be synthesized by analogous processes disclosed in the Hungarian patent specifications Nos. 179,018, 191,702, 194,529 and 194,550.

The compounds of general formula (I), wherein (A) represents a group of general formula (c), are advantageously prepared by converting the 4-methyl group of the corresponding 4-methyl-5H-2,3-benzodiazepine derivative to in aldehyde group e. g. by oxidation with selenium dioxide, then reducing the aldehyde group with sodium borohydride to a hydroxymethyl group. In the obtained compound of general formula (III), wherein Z stands for a —$CH_2OH$ group, the hydroxy group is converted into an amino group by the Mitsunobu reaction (O. Mitsunobu: Synthesis 1, 1981). Namely, the compound of general formula (III), wherein Z represents a hydroxymethyl group, is reacted under the known reaction conditions with phthalimide, the resulting phthalimidomethyl group is converted to the aminomethyl group by hydrazinolysis, or in the Mitsunobu reaction the hydroxymethyl compound is first transformed into the azidomethyl compound, then by methods known from the literature the azido group is reduced or treated with triphenylphosphine to yield the amino group. The ring closure of the compounds obtained after acylating the 4-aminomethyl-2,3-benzodiazepine derivatives is carried out preferably by a reaction with e. g. phosphorus oxychloride.

The compounds of general formula (I), wherein (A) means a group of general formula (d), are prepared by reacting the above 4-methyl-5H-2,3-benzodiazepine derivatives with a 3-halo-2-oxo-carboxylic acid ester of general formula (VI), e. g. ethyl bromo-pyruvic acid or α-haloketones. The reactions are performed on the basis of analogue ring closing reactions known from the literature [e. g. C. Casagrande et al.: J. Med. Chem. 11, 765 (1968); C. Galera et al.: J. Het. Chem. 23, 1889 (1986); Y. Blache et al.: J. Het. Chem. 32, 1317 (1995)].

In the compounds of general formula (I) the reduction of the nitro group is usually carried out in polar solvents, at room temperature or at higher temperatures, in the presence of Raney-nickel, platinum or palladium catalysts. In addition to hydrogen gas hydrazine hydrate, ammonium formate or cyclohexene may serve as hydrogen sources. Optionally the amino group can be transformed further by known methods, e. g. alkylation, acylation or in a Sandmeyer reaction.

The AMPA antagonistic effect of the compounds of general formula (I) is confirmed by the following studies.
Inhibition of AMPA Receptors Two experimental models were applied to demonstrate the inhibitory effect of the compounds of general formula (I) on AMPA receptor activation. In the first model the "spreading depression" inducing effect of glutamate agonists was studied, while in the second model the transmembrane ion current induced by the activation of glutamate receptors was directly measured.

Inhibition of AMPA and Kainate Induced "Spreading depression" in the Isolated Chicken Retina Preparation The kainate and AMPA antagonizing effect was studied in vitro in the retinal "spreading depression" model [M. J. Sheardown: Brain Res. 607, 189 (1993)]. The AMPA/kainate antagonists extend the latency of the kainate (5 $\mu$M) or AMPA (5 $\mu$M) induced development of "spreading depression".

In the chicken retina model the kainate induced "spreading depression" was inhibited by the compounds of the invention at $IC_{50}$ values of 0.5 and 5 $\mu$M. The $IC_{50}$ value of the compound of Example 17 amounted to 2.5 $\mu$M while those of Examples 18 and 35 amounted to 0.5 and 0.98 $\mu$M, resp. The response to AMPA could usually be inhibited slightly less and the major part of $IC_{50}$ values was in the range of 3–15 $\mu$M. Thus the AMPA induced "spreading depression" was inhibited by the compound of Example 17 at an $IC_{50}$ value of 7.3 $\mu$M and by compounds of Examples 21 and 27 at $IC_{50}$ values of 4.3 and 3.1 $\mu$M, resp. This demonstrates that the compounds of the invention, beyond strongly inhibiting AMPA receptors, also inhibit an other non-NMDA type glutamate receptor group, the specific kainate receptors.

Inhibition of AMPA and Kainate Induced Transmembrane Currents

The effect of the compound of Example 17 on whole cell currents induced by 100 $\mu$M kainate or 5 $\mu$M AMPA, resp., was studied on Purkinje cells of the cerebellum according to the method of Bleakman et al. [Neuropharmacology 12, 1689 (1996)]. The $IC_{50}$ value against kainate was 4.97 $\mu$M and that against AMPA 2.02 $\mu$M. In this preparation kainate was also exerting its effect through the activation of AMPA receptors. According to the obtained $IC_{50}$ values the ion current induced by AMPA receptor activation is twice as strongly inhibited by the compound of Example 17 than by the reference compound GYKI 52466 having also a 2,3-benzodiazepine structure [5-(4-aminophenyl)-9H-1,3-dioxolo[4,5-h][2,3]-benzodiazepine; Hungarian Patent specification No. 191,698, Example 8], which had $IC_{50}$ values of 8.8 and 11.0, resp.

Anticonvulsive Effect

In the therapy of epilepsy a great variety of drugs is used but unfortunately they have severe side effects, furthermore the disease exists in particular forms which fail to respond to the available drugs. Thus novel antiepileptic drugs are required with a mechanism of action which is different from that of the available drugs. The introduction of drugs acting on the central nervous system by lowering the overactivation by glutamate are awaited with great expectation [TIPS 15, 456 (1994)].

In Table I the anticonvulsive effect of some compounds of the invention in the electroshock test is presented [J. Pharmacol. Exp. Ther. 106, 319 (1952)]. The anticonvulsive effect was also studied in convulsions induced by various chemical agents, e. g. pentetrazole [J. Pharmacol. Exp. Ther 108, 168 (1953)], strychnine [J. Pharmacol. Exp. Ther. 129, 75 (1960)], bemegride, nicotine, bicuculline, 4-aminopyridine and 3-mercaptopropionic acid. The pretreatment period was 60 minutes. The test compounds were administered orally in 3 doses to 10 male CD 1 mice in each dose group. The results are presented in Table 1.

TABLE 1

Anticonvulsive effect in mice $ED_{50}$ (mg/kg, p.o.)

| Compound Example No. | ES | Pentetrazole | Stryclinine | Bemegride | Nicotine | Bicuculline | 4-AP | 3-MPA |
|---|---|---|---|---|---|---|---|---|
| Phenytoin | 10 | >400 | 160 | >200 | 12 | — | — | — |
| GYKI-52466 | 38 | 115 | 87 | 73 | 70 | 35 | 43 | 47 |
| 17 | 24 | 54 | 67 | 41 | 13 | 23 | 55 | 38 |
| 20 | 44 | ~100 | >100 | — | ~25 | ~25 | ~50 | 50–100 |
| 27 | 24 | 62 | 44 | 40 | 18 | 22 | 7 | 67 |

Abbreviations:
ES = electroshock
4-AP = 4-aminopyridine
3-MPA = 3-mercaptopropionic acid The above data demonstrate the significant anticonvulsive effect of the compounds of general formula (I) in the ES test. The compound of Example 17 has a broad spectrum anticonvulsive effect even compared to phenytoin, a drug widely used in therapy.

Muscle Relaxant Effect

In clinical practice central muscle relaxants are used when the tonicity of skeletal muscles is increased due to muscle injury, trauma of the spinal cord or brain, or some chronic degenerative disease, and hyperreflexia or tremor develops. Muscle spasms are often painful and inhibit normal motility.

The muscle relaxant activity of the compounds of general formula (I) was measured in the "inclined screen" test of Randall [J. Pharmacol. Exp. Ther. 129, 163 (1960)] and in the rotarod test [J. Am. Pharm. Assoc. 46, 208 (1975)]. The compounds were administered in 3 i. p. doses to ten CD 1 mice in each dose group. The muscle relaxant activity of the compounds of the invention was demonstrated by the results obtained with the compounds of Examples 17 and 27 (Table 2).

TABLE 2

Muscle relaxant activity in mice

| Compound Example No. | Inclined screen $ED_{50}$ i. p. (mg/kg) | Rotarod $ED_{50}$ i. p. (mg/kg) |
|---|---|---|
| Baclofen | 26 | 13 |
| GYKI 52466 | 47 | 24 |
| 17 | 36 | 16 |
| 27 | 47 | 14 |

The efficacy of the compounds of general formula (I) in the above muscle relaxant tests demonstrates that they can have therapeutic value in treating diseases where increased muscular tone is the problem to be solved.

Inhibition of Focal Ischemia

The focal ischemia inhibiting effect of the compound of Example 17 was studied on the "middle cerebral artery occlusion" (MCAO) test in anesthesized rats. The blood supply of the arteria cerebri media was transitorily inhibited with an intralaminarly introduced embolus, then perfusion was reinstated by removing the embolus and thus a human "stroke" like status was induced in an experimental animal model, in rats. After histological processing the developed infarcted area was measured by a computerized scanner program [R. T. Bartus: Stroke 11, 2265 (1994) and S. G. Sydserff: Brit. J. Pharmacol. 114, 1631 (1995)]. The results obtained are presented in Table 3.

TABLE 3

Inhibition of focal ischemia in rats

| Compound Example No. | Dose (mg/kg) i. v. | N | Score of infarcted area | Change % |
|---|---|---|---|---|
| a) Size of infarcted area | | | | |
| Vehicle | — | 10 | 40518 ± 5924 | |
| 17 | 6 × 1 | 7 | 16122 ± 4368* | −60.2 |
| 17 | 6 × 2 | 10 | 13229 ± 2313* | −67.4 |
| b) Infarcted area in percent of cerebral hemisphere | | | | |
| Vehicle | — | 10 | 33.7 ± 4.94 | |
| 17 | 6 × 1 | 7 | 13.4 ± 3.64* | |
| 17 | 6 × 2 | 10 | 11.0 ± 1.93* | |

N = number of animals.
*= calculated by the Dunnet test after e. g. 0.01 ANOVA [C. W. Dunnet: J. Amer. Statist. Ass. 50, I096-0021 (1955)].

In the above experiment the rate of cerebral cell damage, induced by the occlusion of the middle cerebral artery, was significantly reduced by 6×1 mg/kg i. v. doses of the compound of Example 17 in the best human stroke animal model.

Based on the above pharmacological results the compounds of general formula (I) according to the invention can influence the dysfunctions of the AMPA receptors. Thus the compounds according to the invention are suitable for the treatment of neurological and psychiatric disorders induced by the extremely increased activation of the AMPA receptor. Consequently in therapy they can be applied as muscle relaxants, anticonvulsive and neuroprotective agents. They possess therapeutic value in the treatment of epilepsy, diseases associated with spasms of the skeletal muscles, acute and chronic neurodegenerative disorders, e. g. cerebral ischemia (stroke).

Neurological diseases which can be prevented or treated in this way are the following: Parkinson's disease, Alzheimer's disease, Huntington chorea, amyotrophic lateral sclerosis, olivopontocerebellar atrophy, AIDS dementia and senile dementia. They are also suitable for the treatment of neurodegenerative states developed as a result of cerebrovascular disasters (stroke, cerebral and spinal traumas), hypoxia, anoxia or hypoglycemic states, resp. The compounds of the invention can be advantageously applied for the treatment of various psychiatric diseases, e. g. anxiety, schizophrenia, sleeping disorders, alleviation of symptoms of alcohol, drug and narcotics withdrawal. They can be beneficial in preventing the development of tolerance against sedative drugs and pain killers.

They are assumed to be suitable drugs in epileptic diseases, in the treatment of muscle spasms of central origin and in the alleviation of pathological pain.

For therapeutic use the compounds of general formula (I) of the invention can be converted into enteral or parenteral pharmaceutical compositions. For this purpose organic and inorganic carriers and auxiliary materials are employed, e. g. water, gelatin, acacia gum, lactose, starch, magnesium stearate, talc, vegetable oil, polyethyleneglycols, etc.

The pharmaceutical composition can be prepared in solid form, e.g. tablet, coated tablet, suppository or capsule form or also in liquid form, e. g. solution, suspension or emulsion form. The above auxiliary materials can be also supplemented with other additives, such as preservatives, stabilizing, emulsifying agents, buffers, etc.

For parenteral use the active ingredient is prepared in the form of sterile solution or suspension. The sterile vehicle can contain in addition adjuvants such as a local anesthetic agent, stabilizing agent or buffer, resp. The dosage of the active ingredient depends on the route of administration, the type and severity of the disease as well as the mass and age of the patient. The daily dose can be 0.5–1000 mg, preferably 20–200 mg, in a single dose or divided in several doses.

The compounds according to the invention and the process for their preparation are illustrated in detail by the following non-limiting Examples.

EXAMPLES 1–7

General Method for Preparing Compounds of General Formula (I), wherein X=H, Y=Cl, $R^1$=4-nitro Group, $R^2$=H and A Represents a Group of General Formula (a)

10 mM of 8-chloro-1-(4-nitrophenyl)-3H-4,5-dihydro-2,3-benzo-diazepin-4-thione were refluxed for 1–10 hours in ethyleneglycol monomethyl ether with 11–20 mM of aminoacetal or aminoketal of general formula (IV) and 10 mM of red mercury oxide. The reaction mixture was filtered, evaporated and purified on a Kieselgel column using a mixture of chloroform-methanol (98:2) as eluant.

The obtained condensation product was refluxed for 1–2 hours in 1:1 mixture of concentrated hydrochloric acid and ethanol, yielding the product presented in Table 4 in hydrochloride form.

Products isolated as bases are suitably prepared as follows: the above condensation product is stirred for 1–2 hours with methanesulfonic acid, the reaction mixture is diluted with water and made alkaline with 5 M sodium hydroxide, finally the formed crystalline product is filtered.

Compounds of general formula (I) prepared by the above process are presented in Table 4.

TABLE 4

| Example No. | $R^3$ | $R^4$ | Reagent | Yield % | M.p. ° C. (HCl salt) |
|---|---|---|---|---|---|
| 1 | H | H | 2-Aminomethyl--1,3-dioxolane | 48 | 210–215 |
| 2 | Me | H | 2-(1-Aminoethyl)-1,3--dioxolane | 34 | 215–220 |
| 3 | H | Me | 2-Aminomethyl-2-methyl-1,3-dioxolane | 41 | 205–208 |
| 4 | Me | Me | 2-(1-Aminoethyl)-2--methyl-1,3-dioxolane | 46 | 207–210 |
| 5 | Et | H | 2-(1-Aminopropyl)-1,3--dioxolane | 20 | 150–153 |
| 6 | H | 4-NO$_2$--phenyl | 2,2-Diethoxy-2-(4-nitro-phenyl)-ethylamine | 30 | 270–272* |
| 7 | H | 4-Pyri--dyl | 2,2-Diethoxy-2-(4-pyri-dyl)-ethylamine | 30 | 250–252* |

*Base

Starting compounds of Examples 1–7 can be prepared as follows:

Step a)
7-Chloro-1-(4-nitrophenyl)-isochromane 24.97 g (160 mM) of 2-(4-chlorophenyl)-ethanol and 24.17 g (160 mM) of 4-nitrobenzaldehyde were dissolved in 480 ml of anhydrous benzene, then 21.76 g (160 mM) of anhydrous zinc chloride were added. Dry HCl gas was led into the stirred suspension for 4 hours and stirring was continued overnight. The reaction mixture was first washed with water then with a solution of sodium bisulfite, dried, filtered and finally evaporated. The residue was recrystallized from ethanol.

Yield 26.2 g (56%), m. p. 98–101° C.

Step b)
4-Chloro-2-(4-nitrobenzoyl)-phenylacetic acid 26.1 g (90 mM) of 7-chloro-1-(4-nitrophenyl)-isochromane were dissolved in 360 ml of acetone, then 260 ml of Jones reagent were added and the reaction mixture was stirred for 16 hours. The precipitated chromic sulfate was filtered and the filtrate was evaporated. The evaporation residue was treated with 10% aqueous sodium carbonate solution and dichloromethane. The aqueous phase was acidified with 36% hydrochloric acid and the precipitated crystalline product was filtered.

Yield 18.1 g (63%), m. p. 135–139° C.

Step c) 8-Chloro-1-(4-nitrophenyl)-3H-4,5-dihydro-2,3-benzodiazepin-4-one 17.6 g (55 mM) of 4-chloro-2-(4-nitrobenzoyl)-phenylacetic acid and 8 ml of 85% hydrazine hydrate were refluxed in 340 ml of ethanol for 4 hours. The reaction mixture was cooled, acidified with 115 ml of 1 M hydrochloric acid and evaporated. The residue was mixed with 50 ml of water, the crystals were filtered and dried. The resulting hydrazone derivative was dissolved in 300 ml of anhydrous dichloromethane and treated with a solution of 13.4 g (65 mM) of dicyclohexylcarbodiimide in 210 ml of anhydrous dichloromethane. The reaction mixture was stirred at room temperature overnight, then the precipitated crystals were filtered and washed with dichloromethane.

Yield 12.5 g (72%), m. p. 275–278° C.

Step d)
8-Chloro-1-(4-nitrophenyl)-3H-4,5-dihydro-2,3-benzodiazepine-4-thione 12.0 g (38 mM) of 8-chloro-1-(4-nitrophenyl)-3H-4,5-dihydro-2,3-benzodiazepin-4-one and 13.3 g (60 mM) of phosphorus pentasulfide were heated at 80° for 2 hours in 150 ml of anhydrous pyridine. After cooling the reaction mixture was poured on 1 kg of ice, the precipitated crystals were filtered and washed with water. The crude product was recrystallized from ethyleneglycol monomethyl ether.

Yield 8.92 g (71%), m. p. 231–234° C.

EXAMPLES 8–11

General Method for Preparing Compounds of General Formula (I), wherein X=H, Y=Br, $R^1$=4-nitro Group, $R^2$=H and A Represents a Group of General Formula (a)

10 mM of 8-bromo-1-(4-nitrophenyl)-3H-4,5-dihydro-2,3-benzo-diazepine-4-thione were refluxed with 11–20 mM of an aminoacetal or aminoketal of general formula (IV) and 10 mM of red mercury oxide for 1–10 hours, then the process described in Examples 1–7 was applied.

Compounds isolated as bases were processed as reported under Examples 1–7.

Compounds of general formula (I) prepared by the above process are presented in Table 5.

TABLE 5

| Example No. | $R^3$ | $R^4$ | Reagent | Yield % | M.p. ° C. (HCl salt) |
|---|---|---|---|---|---|
| 8 | Me | H | 2-(1-Aminoethyl)-1,3-dioxolane | 28 | 215–220 |
| 9 | H | Me | 2-Aminomethyl-2-methyl-1,3-dioxolane | 50 | 194–202 |
| 10 | Me | Me | 2-(1-Aminoethyl)-2-methyl-1,3-dioxolane | 42 | 212–219 |
| 11 | H | 4-Pyridyl | 2,2-Diethoxy-2-(4-pyridyl)-ethylamine | 60 | Foam* |

*TLC: developed in a mixture of chloroform - methanol (95:5) $R_f$: 0.56

Starting compounds of Examples 8–11 can be prepared as follows:

Step a)
7-Bromo-1-(4-nitrophenyl)-isochromane 20.1 g (100 mM) of 2-(4-bromophenyl)-ethanol and 15.1 g (100 mM) of 4-nitrobenzaldehyde were dissolved in 300 ml of anhydrous benzene, then 13.6 g (100 mM) of anhydrous zinc chloride were added and dry hydrochloric acid gas was led into the stirred mixture for 4 hours. Then the process described under Examples 1–7, Step a) was applied. The crude product was recrystallized from ethyl acetate.

Yield 20.7 g (62%), m. p. 104–107° C.

Step b)
4-Bromo-2-(4-nitrobenzoyl)-phenylacetic acid 20.0 g (60 mM) of 7-bromo-1-(4-nitrophenyl)-isochromane were dissolved in 240 ml of acetone, then 174 ml of Jones reagent were added and the reaction mixture was stirred for 16 hours. Thereafter the process described under Examples 1–7, Step b) was applied.

Yield 13.3 g (61%), m. p. 127–130° C.

Step c)
8-Bromo-1-(4-nitrophenyl)-3H-4,5-dihydro-2,3-benzodiazepin-4-one 12.7 g (35 mM) of 4-bromo-2-(4-nitrobenzoyl)-phenylacetic acid and 5 ml of 85% hydrazine hydrate were refluxed in 210 ml of ethanol for 4 hours. Thereafter the process described under Examples 1–7, Step c) was applied.

Yield 8.19 g (65%), m. p. 264–267° C.

Step d)
8-Bromo-1-(4-nitrophenyl)-3H-4,5-dihydro-2, 3-benzodiazepine-4-thione 7.92 g (22 mM) of 8-bromo-1-(4-nitrophenyl)-3H-4,5-dihydro-2,3-benzodiazepin-4-one and 7.78 g (35 mM) of phosphorus pentasulfide were heated at 80° C. for 2 hours in 90 ml of anhydrous pyridine. Thereafter the process described under Examples 1–7 was applied. The crude product was recrystallized from ethyleneglycol monomethyl ether.

Yield 5.55 g (67%), m. p. 220–223° C.

EXAMPLES 12 and 13

General Method for Preparing Compounds of General Formula (I), wherein X=Cl, Y=Cl, $R^1$=4-nitro Group, $R^2$=H and A Represents a Group of General Formula (a)

10 mM of 7,8-dichloro-1-(4-nitrophenyl)-3H-4,5-dihydro-2,3-benzodiazepine-4-thione were refluxed for 1–10 hours with 11–20 mM of an aminoacetal or aminoketal of general formula (IV) and 10 mM of red mercury oxide, then the process described under Examples 1–7 was applied.

The compounds of general formula (I) prepared by this process are presented in Table 6.

TABLE 6

| Example No. | $R^3$ | $R^4$ | Reagent | Yield % | M.p. °C. (HCl salt) |
|---|---|---|---|---|---|
| 12 | Me | H | 2-(1-Aminoethyl)-1,3-dioxolane | 13 | 221–224 |
| 13 | H | Me | 2-Aminomethyl-2-methyl-1,3-dioxolane | 41 | 240–244 |

Starting compounds of Examples 12 and 13 can be prepared as follows:
Step a)
6,7-Dichloro-1-(4-nitrophenyl)-isochromane
19.1 g (100 mM) of 2-(3,4-dichlorophenyl)-ethanol [G. J. Park et al.: J. Org. Chem. 22, 93 (1957)] and 15.1 g (100 mM) of 4-nitrobenzaldehyde were dissolved in 300 ml of anhydrous benzene, then 13.6 g (100 mM) of anhydrous zinc chloride were added and dry hydrochloric acid gas was led into the stirred suspension for 4 hours. Then the process described under Examples 1–7, Step a) was applied. The crude product was recrystallized from ethanol.
Yield 9.11 g (30%), m. p. 130–132° C.
Step b)
4,5-Dichloro-2-(4-nitrobenzoyl)-phenylacetic acid
8.70 g (26.8 mM) of 6,7-dichloro-1-(4-nitrophenyl)-isochromane were dissolved in 180 ml of acetone, then 78 ml of Jones reagent were added and the reaction mixture was stirred for 16 hours. The precipitated chromium sulfate was filtered, the filtrate was evaporated and the evaporation residue was recrystallized from 96% acetic acid. The obtained crystals were filtered and purified on a Kieselgel column using a mixture of chloroform-methanol (9:1) as eluant.
Yield 5.1 g (54%), m. p. 187–190° C.
Step c)
7,8-Dichloro-1-(4-nitrophenyl)-3H-4,5-dihydro-2,3-benzodiazepin-4-one
6.10 g (17.2 mM) of 4,5-dichloro-2-(4-nitrobenzoyl)-phenylacetic acid and 6 ml of 85% hydrazine hydrate were refluxed in 300 ml of 2-propanol for 6 hours. The reaction mixture was evaporated and the residue was dissolved in a mixture of 45 ml 40% acetic acid and 400 ml of dichloromethane. The mixture was separated and the dichloromethane phase was washed with water, dried, then 3.60 g (17.5 mM) of dicyclohexyl-carbodiimide were added to the stirred solution. The reaction mixture was stirred at room temperature overnight, the formed precipitate was filtered and the filtrate was evaporated. The evaporation residue was refluxed in 120 ml of methanol and the hot mixture was filtered.
Yield 4.40 g (73%), m. p. 268–270° C.
Step d)
7,8-Dichloro-1-(4-nitrophenyl)-3H-4,5-dihydro-2.3-benzodiazepine-4-thione
2.21 g (6.31 mM) of 7,8-dichloro-1-(4-nitrophenyl)-3H-4,5-dichloro-2,3-benzodiazepin-4-one and 2.24 g (10.1 mM) of phosphorus pentasulfide were heated at 82° C. for 3 hours in 50 ml of anhydrous pyridine. Thereafter the process described under Examples 1–7, Step d) was applied. The crude product was recrystallized from ethyleneglycol monomethyl ether.
Yield 1.41 g (61%), m. p. 210–213° C.

EXAMPLES 14 and 15

General Method for Preparing Compounds of General Formula (I), wherein X=H, Y=Br, $R^1$=2-Cl, $R^2$=H and A Represents a Group of General Formula (a)

2 mM of 8-bromo-1-(2-chlorophenyl)-3H-4,5-dihydro-2,3-benzodiazepine-4-thione were refluxed for 1–2 hours with 2.2–4 mM of an aminoacetal or aminoketal of general formula (IV) and 2 mM of red mercury oxide in ethyleneglycol monomethyl ether. The mercury sulfide was filtered and the filtrate evaporated. The obtained condensation product was refluxed for 1–2 hours in a mixture of concentrated hydrochloric acid and ethanol (1:1), then the mixture was evaporated. The crystalline residue was recrystallized from ethanol.

The compounds of general formula (I) prepared by this process are presented in Table 7.

TABLE 7

| Example No. | $R^3$ | $R^4$ | Reagent | Yield % | M.p. °C. (HCl salt) |
|---|---|---|---|---|---|
| 14 | Me | H | 2-(1-Aminoethyl)-1,3-dioxolane | 21 | 132–140 |
| 15 | H | Me | 2-Aminomethyl-2-methyl-1,3-dioxolane | 48 | 210–215 |

EXAMPLES 16–28

General Method for Preparing Compounds of General Formula (I), wherein $R^1$=4-amino Group, $R^2$=H, A Represents a Group of General Formula (a) and X, Y, $R^3$ and $R^4$ Represent Moieties Presented in Table 8

2 mM of a compound of general formula (I), wherein $R^1$ represents a 4-nitrophenyl group, furthermore $R^2$, $R^3$, $R^4$, X and Y have the same meaning as above, were dissolved in a mixture of methanol and dichloromethane, then stirred for 1–5 hours with 8–10 mM of 85–98% hydrazine hydrate and 0.1–2 g of Raney-nickel catalyst at 20–40° C. The catalyst was filtered off and the filtrate was evaporated. The crude product was recrystallized from ethanol. The compounds of general formula (I) prepared by this process are presented in Table 8.

TABLE 8

| Example No. | X | Y | $R^3$ | $R^4$ | Starting compound Example No. | Yield % | M.p. °C. |
|---|---|---|---|---|---|---|---|
| 16 | H | Cl | H | H | 1 | 67 | 210–214 |
| 17 | H | Cl | Me | H | 2 | 79 | 229–230 |
| 18 | H | Cl | H | Me | 3 | 71 | 267–270 |
| 19 | H | Cl | Me | Me | 4 | 83 | 274–278 |
| 20 | H | Cl | Et | H | 5 | 72 | 247–250 |
| 21 | H | Cl | H | 4-$NH_2$-phenyl | 6 | 84 | 250–253 |
| 22 | H | Cl | H | 4-Pyridyl | 7 | 68 | 293–294 (d) |
| 23 | H | Br | Me | H | 8 | 64 | 248–251 |
| 24 | H | Br | H | Me | 9 | 77 | 263–268 |
| 25 | H | Br | Me | Me | 10 | 84 | 272–275 |
| 26 | H | Br | H | 4-Pyridyl | 11 | 41 | 295–300 (d) |
| 27 | Cl | Cl | Me | H | 12 | 40 | 254–255 |
| 28 | Cl | Cl | H | Me | 13 | 71 | 284–286 |

EXAMPLES 29–32

General Method for Preparing Compounds of General Formula (I), wherein X=H, Y=Cl, $R^1$=4-nitro group, $R^2$=H and A Represents a Group of General Formula (b)

10 mM of 8-chloro-4-methylthio-1-(4-nitrophenyl)-5H-2,3-benzodiazepine were reacted in dimethylformamide at 120–130° C. for 9–15 with 20–25 mM of an acyl hydrazide of general formula (V) in the presence of 0.5 mM of concentrated hydrochloric acid. The reaction mixture was poured on crushed ice, then the crude product was filtered and purified by recrystallization.

The compounds of general formula (I) prepared by this process are presented in Table 9.

TABLE 9

| Example No. | $R^5$ | Yield % | M. p. ° C. |
|---|---|---|---|
| 29 | Methyl | 72 | 271–274 |
| 30 | 4-Pyridyl | 86 | 287–289 |
| 31 | 4-Nitrophenyl | 68 | 287–290 |
| 32 | Methoxymethyl | 88 | 266–268 |

Starting compounds of Examples 29–32 can be prepared as follows:

To a solution of 10 mM of 8-chloro-1-(4-nitrophenyl)-5H-2,3-benzodiazepine-4-thione [Example 1–7, Step d)] in acetone 20 mM of potassium carbonate and 30 mM of methyliodide were added and the reaction mixture was stirred at room temperature for 3 hours. The product was filtered, washed with water and purified by recrystallizing from dimethylformamide.

Yield 82%, m. p. 249–252° C.

EXAMPLES 33–36

General Method for Preparing Compounds of General Formula (I), wherein X=H, Y=Cl, $R^1$=4-amino Group, $R^2$=H and A Represents a Group of General Formula (b)

10 mM of a compound of general formula (I), wherein X=H, Y=Cl, $R^1$=4-nitro group, $R^2$=H, A represents a group of general formula (b) and $R^5$ represents a group listed in Table 9, described in Examples 29–32, were dissolved in a mixture of methanol and dichloromethane and stirred for 1–5 hours with 35–45 mM of 85–98% hydrazine hydrate and 0.5–2.0 g of Raney-nickel catalyst at 20–40° C. The catalyst was filtered off and the filtrate was evaporated. The crude product was purified by recrystallization or column chromatography.

The compounds of general formula (I) prepared by this process are presented in Table 10.

TABLE 10

| Example No. | $R^5$ | Yield % | M. p. ° C. |
|---|---|---|---|
| 33 | Methyl | 91 | 228–231 |
| 34 | 4-Pyridyl | 92 | 284–288 |
| 35 | 4-Aminophenyl | 85 | 191–193 |
| 36 | Methoxymethyl | 83 | 195–197 |

EXAMPLE 37

6-(4-Acetylaminophenyl)-8-chloro-2-methyl-11H-imidazo[1,2-c][2,3]-benzodiazepine The solution of 0.46 g (1.42 mM) of the compound described in Example 17 in 8 ml of anhydrous pyridine was stirred with 0.20 ml of acetylchloride for 1.5 hours at 5–10° C. The reaction mixture was poured on crushed ice, the precipitated product was filtered and recrystallized from ethanol.

Yield 0.33 g (63%), m. p. 265–266° C.

EXAMPLE 38

6-Phenyl-8-chloro-3-methyl-11H-imidazo[1,2-c][2,3]-benzodiazepine

The solution of 1.10 g (3.2 mM) of the compound described in Example 18 was treated in 12 ml of dimethylformamide with 0.8 ml of isoamyl nitrite at 65° C. The reaction mixture was diluted with 5 M hydrochloric acid and extracted with ether. The ether layer was evaporated and purified on a Kieselgel column using a mixture of chloroform and methanol (98:2) as eluant.

Yield 0.39 g (39%), m. p. 166–169° C.

EXAMPLE 39

2-Ethoxycarbonyl-8-chloro-6-(4-nitrophenyl)-11H-pyrrolo[1,2-c][2,3]-benzodiazepine The solution of 0.50 g (1.6 mM) of 8-chloro-4-methyl-1-(4-nitrophenyl)-5H-2,3-benzodiazepine and 0.27 ml (2.2 mM) of ethyl bromopyruvic acid in 20 ml of ethanol was refluxed for 12 hours. The reaction mixture was evaporated and the product was purified on a silicagel column applying benzene as eluant.

Yield 0.29 g (44%) of the aimed product which was used in the next reaction without further purification.

The starting compound of this Example was prepared as follows:

Step a)

7-Chloro-3-methyl-1-(4-nitrophenyl)-isochromane 11.94 g (70 mM) of 1-(4-chlorophenyl)-2-propanol [J. Med. Chem. 21, 454 (1978)] and 10.57 g (70 mM) of 4-nitrobenzaldehyde were dissolved in 70 ml of anhydrous benzene, then 9.56 g (70 mM) of freshly prepared anhydrous zinc chloride were added and dry hydrochloric acid gas was led into the mixture for 3 hours. Then the mixture was refluxed for 1.5 hours, cooled, diluted with water and the layers were separated. The organic layer was first washed with water then with a solution of sodium hydrogen carbonate, dried and evaporated. The resulting crude product was recrystallized from ethanol.

Yield 6.8 g (32%), m. p. 120–123° C.

Step b)

7-Chloro-3-methyl-1-(4-nitrophenyl)-2-benzopyrilium perchlorate

To a solution of 6.8 g (22.44 mM) of the isochromane derivative [prepared in the above Step a)] in 70 ml of acetone 29 ml (78 mM) of Jones reagent were added dropwise under ice chilling, during 1 hour and the reaction mixture was stirred for 4 hours at 25° C. The precipitated chromium salt was filtered off, the filtrate was evaporated and the crystalline residue was resuspended in water and repeatedly filtered. The resulting crystalline product was dissolved in 76 ml of hot glacial acetic acid, 1.48 ml of 70% perchloric acid were added, after chilling the precipitated crystalline product was filtered and washed several times with small portions of glacial acetic acid.

Yield 3.73 g (42%), m. p. 247–255° C.

Step c)

8-Chloro-4-methyl-1-(4-nitrophenyl)-5H-2,3-benzodiazepine 4.1 g (10.25 mM) of benzopyrilium perchlorate, prepared according to the above Step b, were added to a mixture of 20.5 ml of dimethylformamide and 1.5 ml (70.7 mM) of 98% hydrazine hydrate while cooling with water The reaction mixture was stirred for 1.5 hours at 25° C., then 25 ml of water were added, the precipitated crude product was filtered and washed with water. The resulting crude product was recrystallized from 25 ml of isopropanol.

Yield 2.82 g (87%), m. p. 199–203° C.

EXAMPLE 40

6-(4-Aminophenyl)-2-ethoxycarbonyl-8-chloro-11H-pyrrolo[1,2-c][2,3]-benzodiazepine 0.29 g (0.7 mM) of 2-ethoxycarbonyl-8-choro-6-(4-nitrophenyl)-11H-pyrrolo[1,2-c][2,3]-benzodiazepine (Example 39) was reduced according to the general method described in Examples 16–28.

Yield 0.11 g (41%), m. p. 247–249° C.

EXAMPLE 41

8-Chloro-3-methyl-6-(4-nitrophenyl)-11H-imidazo[3,4-c][2,3]-benzodiazepine 0.59 g (1.6 mM) of 4-(acetaminomethyl)-8-chloro-1-(4-nitrophenyl)-5H-2,3-benzodiazepine [Step e)] was dissolved in 30 ml of anhydrous dichloroethane, then 0.73 ml (7.95 mM) of phosphorus oxychloride were added and the reaction mixture was refluxed for 3 hours.

Thereafter the solution was mixed under ice-chilling with a solution of sodium hydrogen carbonate, the layers were separated, the organic layer was washed with water, dried and evaporated. The crude product, an oil, was purified on a silicagel column using a mixture of ethyl acetate and benzene (4:1) as eluant.

Yield 0.24 g (43%) of a foam which was used without further purification in the reduction reaction (Example 42).

The starting compound of this Example was prepared as follows:
Step a)
4-Formyl-8-chloro-1-(4-nitrophenyl)-5H-2,3-benzodiazepine 9.17 g (29.0 mM) of 8-chloro-4-methyl-1-(4-nitrophenyl)-5H-2,3-benzodiazepine (prepared according to the method described in Example 39) were dissolved in 120 ml of dioxane, then 2.27 g (20.5 mM) of selenium dioxide powder were added and the mixture was stirred on a 90° C. water bath for 40 minutes. Then the solution was treated with active carbon, filtered and poured into 1500 ml of water. The precipitated crystals were filtered and washed with water. The crude product was purified on a Kieselgel column using benzene as eluant.

Yield 2.8 g (29%), m. p. 208–210° C. (decomp.).
Step b)
4-(Hydroxymethyl)-8-chloro-1-(4-nitrophenyl)-5H-2,3-benzodiazepine 2.15 g (6.6 mM) of 4-formyl-8-chloro-1-(4-nitrophenyl)-5H-2,3-benzodiazepine [prepared according to Step a)] were dissolved in 88 ml of a mixture of tetrahydrofuran and water (1:1), then under ice chilling 0.12 g (3.3 mM) of sodium borohydride was added portion-wise. The reaction mixture was stirred at 25° C. for 40 minutes then it was diluted with 90 ml of water. The precipitated crystals were filtered and purified on a Kieselgel column using a mixture of benzene and ethyl acetate (1:1) as eluant.

Yield 1.62 g (75%), gradually decomposing from 163° C. on.
Step c)
4-(Phthalimidomethyl)-8-chloro-1-(4-nitrophenyl)-5H-2,3-benzodiazepine 1.62 g (4.9 mM) of the 4-(hydroxymethyl) derivative [Step b)], 2.54 g (9.7 mM) of triphenylphosphine and 1.42 g (9.7 mM) of phthalimide were dissolved in 72 ml of anhydrous tetrahydrofuran, then a solution of 1.52 ml (9.7 mM) of diethyl azodicarboxylate in anhydrous tetrahydrofuran were added dropwise and the reaction mixture was stirred for 3 hours. After evaporation the resulting residue was recrystallized from 20 ml of ethanol.

Yield 1.34 g (60%), m. p. 254–256° C. (decomp.).
Step d)
4-(Aminomethyl)-8-chloro-1-(4-nitrophenyl)-5H-2,3-benzodiazepine 1.34 g (2.9 mM) of the 4-(phthalimidomethyl) derivative [Step c)] and 1.09 ml (21.7 mM) of 98% hydrazine hydrate were refluxed in 134 ml of methanol for 4 hours. The reaction mixture was evaporated, the residue was mixed with 50 ml of dichloromethane and the precipitate was filtered. The filtrate was evaporated, the residue was suspended in water and filtered.

Yield 0.97 g (100%), m. p. 105–107° C. (decomp.) which was used without further purification in the next reaction step.
Step e)
4-(Acetaminomethyl)-8-chloro-1-(4-nitrophenyl)-5H-2,3-benzodiazepine 0.97 g (3.0 mM) of the 4-(aminomethyl) derivative prepared according to Step d) was stirred for 2 hours with 8 ml of acetic anhydride. Then the reaction mixture was diluted with 40 ml of water, the precipitated crystals were filtered and the crude product was subjected to silicagel column chromatography using a 4:1 mixture of ethyl acetate and benzene as eluant.

Yield 0.59 g (54%), m. p. 216–218° C. (decomp.).

EXAMPLE 42

6-(4-Aminophenyl)-8-chloro-3-methyl-11H-imidazo[3,4c][2,3]-benzodiazepine 0.24 g (0.7 mM) of 8-Chloro-3-methyl-6-(4-nitrophenyl)-11H-imidazo[3,4-c][2,3]-benzodiazepine (Example 41) was reduced according to the general process of Examples 16–28). The crude product was purified by refluxing with ethanol.

Yield 0.12 g (56%), m. p. 256–258° C. (decomp.).

EXAMPLE 43

2-Phenyl-8-chloro-6-(4-nitrophenyl)-11H-imidazo[1,2-c][2,3]-benzodiazepine 1.99 g (6.0 mM) of 8-chloro-1-(4-nitrophenyl)-3H-4,5-dihydro-2,3-benzodiazepine-4-thione were reacted with 1.79 g (12.0 mM) of 2,2-dimethoxy-1-phenyl-ethylamine [W. R. Boon: J. Chem. Soc. 2146 (1957)] according to the process described in Examples 1–7. The resulting condensation product was purified on a Kieselgel column using a mixture of chloroform and methanol (98:2) as eluant, then it was treated with methanesulfonic acid and the product was isolated as a base according to the method described in Examples 1–7.

Yield 0.70 g (28%), m. p. 230–232° C.

EXAMPLE 44

6-(4-Aminophenyl)-2-phenyl-8-chloro-11H-imidazo[1,2-c][2,3]-benzodiazepine 0.62 g (1.5 mM) of 2-phenyl-8-chloro-1-(4-nitrophenyl)-11H-imidazo[1,2-c][2,3]-benzodiazepine was reduced according to the process described in Examples 16–28 and the crude product was recrystallized from 90% isopropanol.

Yield 0.47 g (81%), m. p. 223–226° C.

What is claimed is:

1. A compound of the formula (I), a stereoisomer or an acid addition salt thereof,

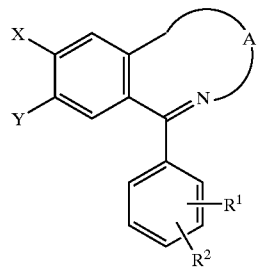

(I)

where $R^1$ and $R^2$ represent independently hydrogen, halogen, a $C_{1-4}$ alkyl, $C_{1-4}$ alkoxy, nitro, trifluoromethyl group or a group of the formula —$NR^8R^9$, wherein $R^8$ and $R^9$ represent independently hydrogen, a $C_{1-4}$ alkyl group or a group of the formula —$COR^{10}$, wherein $R^{10}$ represents hydrogen, an optionally substituted $C_{1-4}$ alkyl group, $C_{6-10}$ aryl group, $C_{1-4}$ alkoxy group, $C_{3-5}$ cycloalkyl group, $C_{2-6}$ alkenyl group, $C_{3-5}$ cycloalkoxy group or a group of the formula —$NR^{11}R^{12}$, wherein $R^{11}$ and $R^{12}$ represent independently hydrogen, a $C_{1-4}$ alkyl group, $C_{3-5}$ cycloalkyl group or $C_{6-10}$ aryl group, x represents hydrogen or chlorine atom, Y represents chlorine or bromine atom, A represents a group of the formula (a) or (c)

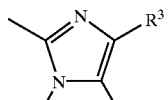

(a)

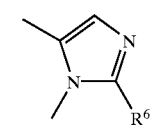

(c)

wherein $R^3$, $R^4$ and $R^6$ represent independently hydrogen, a $C_{1-4}$ alkyl group, $C_{3-5}$ cycloalkyl group, $C_{2-4}$ alkenyl group, $C_{2-4}$ alkinyl group or $C_{6-10}$ aryl group which can optionally be substituted by one or more halogen, nitro, alkoxy, or amino groups;

a heteroaryl group selected from the group consisting of thienyl, furyl and pyridyl;

a group of the formula —$COOR^{13}$ or —$CONR^{14}R^{15}$, wherein $R^{13}$ represents hydrogen or $C_{1-4}$ alkyl group, $R^{14}$ and $R^{15}$ represent independently hydrogen or a $C_{1-4}$ alkyl group.

2. A pharmaceutical composition comprising a compound as claimed in claim 1, together with solvents, diluents, carriers or filling materials usually employed in the preparation of drug formulations.

3. A method for treating epilepsy comprising administering to a subject in need of such treatment an effective amount of the composition of claim 2.

4. A method for reducing excitotoxicity associated with neurodegeneration of excitotoxic origin comprising administering to the subject in need of such treatment an effective amount of the composition of claim 2.

5. A method for reducing excitotoxicity in a neurodegenerative disease selected from the group consisting of cerebral ischemia (stroke), Parkinson's disease, Alzheimer's disease and amyotropic lateral sclerosis comprising administering to the subject in need of such treatment an effective amount of the composition of claim 2.

6. A method of reducing muscle spasms comprising administering to the subject in need of such treatment an effective amount of the composition of claim 2.

7. 6-(4-Aminophenyl)-8-chloro-2-methyl-11H-imidazo[1,2-c][2,3]-benzodiazepine and its acid addition salts.

8. 6-(4-Aminophenyl)-8-chloro-3-methyl-11H-imidazo[1,2-c][2,3]-benzodiazepine and its acid addition salts.

9. 6-(4-Aminophenyl)-8-bromo-2-methyl-11H-imidazo[1,2-c][2,3]-benzodiazepine and its acid addition salts.

10. 6-(4-Aminophenyl)-8,9-dichloro-2-methyl-11H-imidazo[1,2-c][2,3]-benzodiazepine and its acid addition salts.

* * * * *